United States Patent [19]

Neumiller

[11] 4,294,821

[45] Oct. 13, 1981

[54] ODOR ABSORBING COMPOSITIONS

[75] Inventor: Phillip J. Neumiller, Racine County, Wis.

[73] Assignee: S. C. Johnson & Son, Inc., Racine, Wis.

[21] Appl. No.: 216,411

[22] Filed: Dec. 15, 1980

[51] Int. Cl.$^2$ .................. A61L 13/00; A61L 9/01
[52] U.S. Cl. ........................ 424/45; 424/65; 424/76; 424/DIG. 5; 252/426
[58] Field of Search ............... 424/76, 45, 65, DIG. 5; 252/426

[56] References Cited

U.S. PATENT DOCUMENTS

| | | | |
|---|---|---|---|
| 2,900,306 | 8/1959 | Slater | 424/65 |
| 3,131,153 | 4/1964 | Klausner | 424/47 |
| 3,160,555 | 8/1964 | Hamill et al. | 424/45 |
| 3,821,413 | 6/1974 | Hellger, Jr. | 424/76 |
| 4,117,110 | 9/1978 | Hautmann | 424/76 |

Primary Examiner—Donald B. Moyer

[57] ABSTRACT

An odor absorbing composition comprising
(a) from 0.5–45% by weight of diethylene glycol;
(b) from 0.5–45% by weight propylene glycol;
(c) from 0.5–30% by weight triethylene glycol;
(d) from 1–50% by weight glycerine;
(e) from 0.1–20% by weight of a diethanolamide of a $C_{16}$–$C_{18}$ unsaturated fatty acid, and
(f) from 0.05–5% by weight of an unsaturated fatty acid.

10 Claims, No Drawings

ODOR ABSORBING COMPOSITIONS

BACKGROUND OF THE INVENTION

This invention relates to an odor absorbing composition. More particularly this invention relates to an improved composition for removing odors particularly malodors from the air.

The problem of malodors have been with mankind for as long as civilization. There are very few articles or things which do not have some odor associated with them. Often this odor will change over time and the new odor may be undesirable.

Most compositions which treat the air merely mask undesirable odors with the stronger desirable odor. These perfumes and fragrance compositions do not in any way absorb or remove the odors but merely hide or mask the same. Certain compositions such as sodium bicarbonate, activated charcoal, zinc ricinoleate and certain glycols such as ethylene glycol have been utilized as odor absorber compositions in the past. These compositions are somewhat effective. However, they do have difficulties, such as not pulling sufficient odor out of the air, absorbing the odor too slowly or rereleasing the odor from the substrate once it has been absorbed.

One odor absorbing composition is disclosed in West German AS No. 1492372, published Feb. 8, 1973. This publication describes an odor absorbing composition containing an alkylaryl sulfonate and glycerine in a ratio of sulfonate to glycerine of 2:1 to 1:2. This liquid material is impregnated in a filter material.

Belgian Pat. No. 876406 describes a solid granular deodorizing composition comprising siliceous material mixed with perfume and propylene glycol. This material is a dry free-flowing powder which is designed to be used to control odors from cigarettes and the like in sand-filled ashtrays.

U.S. Pat. No. 3,925,021 is a filter arrangement for removing certain gases such as $SO_2$ from the air. In this patent the filters are impregnated with an alkaline substance and a hygroscopic wetting agent such as glycerine, ethylene glycol or propylene glycol.

Soviet Union Certificate No. 544433 discloses an aerosol air deodorant composition including glycerol in an amount from 0.2 to 0.4% along with certain fragrance extracts. Soviet Union Pat. No. 504539 abstracted in Volume 84—169561 Chemical Abstracts discloses a deodorant with increased bactericidal and deodorant properties including 1.5 to 3% triethylene glycol, 4 to 6% propylene glycol, 0.4 to 0.6 glycerol, and various fragrance component materials.

Japanese Pat. Publication 53/101535 describes a deodorant composition comprising glyoxal and an alkyleneglycol. U.S. Pat. No. 2,333,124 describes a method of sterilizing air utilizing glycol as the air sterilant medium. Glycols described in this patent include diethylene glycol, butylene glycol and trimethylene glycol. U.S. Pat. No. 3,160,555 discloses an aerosol disinfecting spray utilizing glycols such as propylene glycol, dipropylene glycol, triethylene glycol, hexylene glycol and resorcinols.

U.S. Pat. No. 3,821,413 discloses an aerosol disinfectant composition including a glycol germicide. U.S. Pat. No. 74,195 describes a method for treating paper cloth and other substrates by utilizing a mixture comprising glycerine and an alkali. U.S. Pat. No. 1,498,797 describes a method of treatment for vegetable parchment by applying a glycol such as ethylene glycol to the parchment. U.S. Pat. No. 2,387,957 describes a method of inhibiting odors utilizing a fluid which is an aqueous solution of salt and glycerine. U.S. Pat. No. 2,443,766 describes a fine resistant dust-collecting composition including a substrate coated with sorbitol, triethylene glycol, water and a wetting agent. Other glycols such as propylene glycols are disclosed. U.S. Pat. No. 3,945,950 describes solid perfume and gels utilizing ethers of diethylene glycol.

BRIEF DESCRIPTION OF THE INVENTION AND OBJECTS AND ADVANTAGES

It has surprisingly been found that an effective odor absorbing composition can be prepared by combining (a) from about 0.5 to about 45% by weight of diethylene glycol; (b) from about 0.5 to 45% by weight propylene glycol; (c) from about 0.5 to 30% by weight triethylene glycol (d) from about 1 to 50% by weight glycerine; (e) from about 0.1 to 20% by weight of a diethanol amide of a $C_{16}$ to $C_{18}$ unsaturated fatty acid, and (f) from about 0.05 to 5% by weight of an unsaturated fatty acid.

The above composition can be used either alone or combined with other active ingredients. Typically this composition will either be impregnated or absorbed on a substrate so as to be able to absorb odors from the surrounding atmosphere or used as a spray from an aerosol or pump spray package.

It is therefore the primary object of the present invention to provide an improved odor-absorbing composition.

It is a further object of the present invention to provide an odor-absorbing composition which performs in a manner superior to the odor-absorbing characteristics of the individual components of the composition.

It is a still further object to provide a composition which can effectively absorb odors when applied as a spray.

It is a still further object of the present invention to provide an odor-absorbing composition which is simple and economical to manufacture which has a high degree of proficiency in removing malodors and other odors from a confined atmosphere.

Still further objects and advantages of the composition of the present invention will become more apparent from the following more detailed description thereof.

DETAILED DESCRIPTION OF THE INVENTION

The odor-absorbing compositions of the present invention comprise: (a) from about 0.5 to 45% by weight of diethylene glycol; (b) from about 0.5 to 45% by weight of propylene glycol; (c) from about 0.5 to 30% by weight triethylene glycol; (d) from about 1 to 50% by weight of glycerine; (e) from about 0.1 to 20% by weight of a diethanol amide of a $C_{16}$ to $C_{18}$ unsaturated fatty acid, and (f) from about 0.05 to 5% by weight of an unsaturated fatty acid.

Although we are not sure of the exact mechanism, it appears that odor in the atmosphere is at least indirectly connected with the moisture in the air. As most of the components in the composition of the present invention are highly hygroscopic, it appears that these materials attract the moisture in the air along with the trapped or entrained malodors. As noted above, while it is known to employ hygroscopic materials to remove moisture and other components from the air, it has been surprisingly found that these materials can be held within a substrate by the composition of the present invention and not re-emit large quantities of the odors and malodors to the atmosphere.

The first component of the composition of the present invention is diethylene glycol. The composition of the present invention must contain from about 0.5 to 45% of diethylene glycol in order to function properly to absorb odors. The diethylene glycol appears to have some solvency for various components of odors. Although the other components of the composition of the present invention will absorb odors if lower or higher amounts of diethylene glycol are present, it has been surprisingly found that within the above range, in combination with the other components of the present invention, an unexpected improvement in odor absorption results. It is preferred to include from 10 to 35% by weight of diethylene glycol in the compositions of the present invention.

The second component of the compositions of the present invention is propylene glycol. This material has been known for use in malodor absorbing compositions. However, it has been surprisingly found that by combining the propylene glycol with the other components of the composition, a surprising improvement in the odor-absorbing properties of the composition of the present invention results. The propylene glycol should be present in amounts of from about 0.5 to 45% by weight. It is preferred to include from 1 to 15% by weight of proplylene glycol in the composition of the present invention.

The third component of the compsition of the present invention is triethylene glycol This material has not been disclosed as an active component in prior odor absorbing material. However, incorporating from about 0.5 to 30% by weight of triethylene glycol into the composition of the present invention results in a surprising increase in absorbent activity. Although the triethylene glycol has little absorbing capacity by itself, it potentiates the absorbing capacity of the other glycols in the composition. It is preferred to incorporate from about 5 to about 20% by weight of triethylene glycol for optimum odor absorbing capacity.

The fourth component of the composition of the present invention is glycerine. Glycerine has been utilized in a number of other compositions as a humectant. However, it has surprisingly been found that the incorporation of from 1 to 50% by weight and preferably 10–40% glycerine in the compositions of the present invention improves the odor-absorbing qualities of the present composition.

The compositions of the present invention must also contain a free unsaturated $C_{16}$ to $C_{18}$ fatty acid in an amount of from about 0.05 to 5% by weight. These acids have the surprising ability to keep the odors absorbed by the composition within the composition and not allow then to regenerate. If the composition does not contain one of these acids, the composition will initially absorb odors effectively, but, after some time has elapsed, will regenerate these odors to the atmosphere. It is preferred to include from about 0.1 to 2% of free unsaturated fatty acid in the composition. Suitable acids include palmitoleic acid, oleic acid, ricinoleic acid, hectadecanoic acid, linoleic acid, linolenic acid, eleosteric acid, etc. The preferred fatty acids are oleic acid, recinoleic acid, hectadecanoic acid and mixtures. The most preferred acid is oleic acid. It is preferred to use from about 0.1 to 2% of free fatty acid in the composition.

As these fatty acids have an unsaturated bond, they are subject to oxidation if exposed to the atmosphere for an extended period of time. The oxidation products often have a malodor which of course defeats the entire purpose of the composition of the present invention. Therefore, it is preferred to add an effective amount of a known anti-oxidant to the composition of the present invention to prevent any reaction of the free fatty acids. Suitable anti-oxidants are described in McCutcheon's Functional Materials 1979 pages 19-22 published 1979 by MC Publishing Co., the disclosure of which is incorporated by reference. Preferred anti-oxidants include Vitamin E, 2,6-di-T-butyl-p-cresol (BHT), a mixture of 2-t-butyl-4-methoxyphenol (BHA) and mixtures thereof.

The compositions of the present invention also include from 0.1 to 20% by weight of a diethanol amide of a $C_{16}$ to $C_{18}$ unsaturated fatty acid. Suitable diethanol amides include the following: diethanolamide of oleic acid, diethanolanolamide of palmitoleic acid, diethanolamide of ricinoleic acid, diethanolamide of linoleic acid, diethanolamide of linolenic acid, diethanolamide of eleosteric acid, etc. and mixtures thereof. Preferred diethanolamides include the diethanolamide of oleic acid, the diethanolamide of ricinoleic acid, diethanolamide of hectadecanoic acid, diethanolamide of mixed $C_{16}$ to $C_{18}$ unsaturated fatty acid and mixtures thereof.

It has been found by the inclusion of the appropriate amount of the diethanolamide into the composition of the present invention that the odor-absorbing qualities of these compositions are remarkably improved. Furthermore, the diethanolamide acts as an emulsifier to hold the components of the composition of the present invention in a homogenious dispersion. It is preferred to utilize from 1 to 7% of this material in the composition.

In addition to the above components a number of other materials can optionally be added into the composition of the present invention. For the most part these compositions are conventional materials which do not adversely affect the odor-absorbing properties of the above materials. One such optional material is zinc ricinoleate, an odor absorbing material. It has been found that incorporation of a small amount of zinc ricinoleate can improve the range of odors which are absorbed by the resultant composition. It should be noted, however, that the composition of the present invention absorbs odor to a much higher degree than zinc ricinoleate alone. Also the compositions of the present invention can include a small amount of perfume. The composition can also contain antifoam agents as aids during manufacturing and dispersing from spray containers.

Although the compositions of the present invention can include a small amount of moisture, i.e., up to 1000 parts per million, the compositions of the present invention function best when the composition is, at least initially, substantially anhydrous, Some of the components are hydroscopic and tend to pick up moisture. However, care should be exercised in the handling and packaging of the compositions to maintain the same in a substantially anhydrous state until use.

The compositions can include up to 99% by weight of a diluent such as alcohols, hydrocarbons, ethylene glycol, etc. Suitable alcohols include methanol, ethanol, propanol, etc. Hydrocarbons must be substantially odorless such as deodorized kerosene, certain isoparrafinic hydrocarbons, etc.

One method of using the compositions of the present invention comprises impregnating from at least 10% by weight of the total composition into a substrate. The upper limit is determined by the capacity of the substrate. It is preferred to add as much of the composition of the present invention to the substrate as possible. For some substrates it is possible to add as much as 200% by weight of the composition of the present invention based on weight of the substrate. This substrate is then packaged in an appropriate container which can be placed within a space to be deodorized.

Substantially any substrate can be utilized in combination with the odor-absorbent composition of the present invention. It is preferred, however, that the substrate be very absorbent so as to trap and maintain the absorbed odors within the substrate and not regenerate the odors. It has been found that the combination of ingredients in the composition of the present invention retard this regeneration of the malodors from the substrate. The individual components when utilized alone will absorb odors to some degree but also they tend to re-emit these odors into the surrounding atmosphere.

The compositions of the present invention may also be dispersed using a pump spray package. In formulating compositions for dispensing the composition of the present invention, it is preferred that anhydrous formulations be used, as substantial moisture has an adverse effect on the odor-absorbing properties of the composition of the present invention. The compositions can be used as is or mixed with from 0 to 99% of a diluent as discussed above.

The aerosol formulations typically contain from 1 to 30% by weight of the composition of the present invention in the final aerosol formulation. This formulation will also include conventional propellants such as the hydrocarbon propellants, propane, butane, isobutane, etc. The flourinated propellants such as propellant 11, 12, 14, etc., chlorinated materials such as 1, 1, 1 trichloroethane, and compressed gases such as carbon dioxide, etc. Generally the propellant content depends on the particular propellant chosen and will range from 5 to 80% by weight. The aerosol formulation also may contain from 10 to 70% by weight of a diluent, provided that the total of propellant and diluent is within the range of 0 to 99%.

The composition of the present invention will now be illustrated by way of the following examples wherein all parts and percentages are by weight and all temperatures are in degrees centigrade.

EXAMPLE 1

One square inch of filter material is impregnated with 1 gram of the following formulation:

| | |
|---|---|
| Glycerine | 37% |
| Diethylene Glycol | 33% |
| Triethylene Glycol | 15% |
| Diethanolamide oleic acid/oleic acid 80/20 | 5% |
| DB 31 Silicone Antifoam | 0.01% |
| Butylated Hydroxy Toluene | 0.01% |
| Propylene Glycol | 9.98% |

The above formulation is mixed together and heated to about 90° C. with agitation to form a solution. The composition forms a clear solution having a yellow color.

The piece of impregnated filter paper is placed in a 1 gallon glass jar along with 0.1 gram onion and a one square inch piece of filter material containing 1.0 gram of water. The jar was sealed for 1 to 2 days and then checked for onion odor. After this time substantially no detectable onion odor was apparent while a similar untreated control, i.e. a glass jar containing an untreated 1 square inch piece of filter paper plus 1 square inch containing 1 gram of water and 0.1 gram onion had a strong onion odor after the same time period.

EXAMPLE 2

The following aerosol formulation is prepared:

| Intermediate A: | |
|---|---|
| Glycerine | 33.5% |
| Diethylene Glycol | 30.5% |
| Triethylene Glycol | 15.0% |
| Diethanol Amide of Oleic Acid/Oleic 80/20 | 5.0% |
| Dioctyl sodium sulfosuccinate (84%) | 5.0% |
| Grillo type H477 | 1.0% |
| DB31 Antifoam | 0.1% |
| Butylated Hydroxy Toluene | 0.1% |
| Propylene Glycol | 9.98% |

The above intermediate was formulated into an aerosol having the following composition:

| | |
|---|---|
| Intermediate A | 15.0% |
| Ethyl Alcohol (SD-40) | 40.0% |
| Isobutane | 36.0% |
| Propane | 9.0% |

When the above aerosol composition is sprayed into a chamber having a foul odor, this odor is neutralized after a short period of time.

EXAMPLES 3–4 and COMPARATIVE EXAMPLE 1

Compositions as set forth in Table I were prepared utilizing the procedure of Example 1.

TABLE I

| | Ex 3 | Ex 4 | Comp Ex 1 | Blank Control |
|---|---|---|---|---|
| Glycerine | 37.0 | 35.0 | 10.0 | — |
| Diethylene Glycol | 33.0 | 35.0 | 40.0 | — |
| Propylene Glycol | 15.0 | 15.0 | 45.0 | — |
| WRS 1-66* | 5.0 | 5.0 | — | — |
| DB31-Antifoam | 0.01 | 0.01 | — | — |
| Triethylene Glycol | 9.98 | 8.99 | — | — |
| Zinc Ricinoleate | — | 1.00 | — | — |
| Butylated Hydroxy Toluene 0.01 | — | — | — | — |
| Clindrol 200-0** | — | — | 5.0 | — |

*WRS 1-66: Mixture of diethanolamide of oleic acid and oleic acid containing from 20 to 27% acid with average of 25%
**Clindrol 200-0: Mixture of diethanolamide of oleic acid and oleic acid containing from 3 to 7% acid with and average of 5%

One gram of each of these formulations is impregnated into a one inch square piece of filter material which is placed into a 1 gallon glass jar along with 0.1 gram of onion and 1 square inch of filter material saturated with 1 gram of water. Each of the jars was randomized and presented to 8 people 48 hours after the samples were placed in the jars. Each panelist was asked to rank the odor in the 4 jars from weakest equaling 1 to strongest equaling 4. The reactions of the 8 panelist shown are in Table II along with the sum of their rankings and the numerical average.

TABLE II

| Panelist | A | B | C | D | E | F | G | H | Sum | Avg. |
|---|---|---|---|---|---|---|---|---|---|---|
| Ex 3 | 1 | 1 | 1 | 1 | 1 | 2 | 1 | 1 | 9 | 1.1 |
| Ex 4 | 3 | 3 | 3 | 3 | 2 | 1 | 2 | 3 | 20 | 2.5 |
| Comp Ex 1 | 2 | 2 | 2 | 2 | 3 | 3 | 3 | 2 | 19 | 2.4 |
| Blank Control | 4 | 4 | 4 | 4 | 4 | 4 | 4 | 4 | 32 | 4.0 |

As is apparent, the composition of Example 3 is by far away superior while there is no significant difference between Example 4 and Comparative Example 1. All three compositions had some reduction in onion odor over the blank control.

EXAMPLE 5

The following formulation was prepared:

| Clindrol 200-0 | 5% |
|---|---|
| Glycerin | 40% |
| Triethylene Glycol | 15% |
| Propylene Glycol | 10% |
| Diethylene Glycol | 29.94% |
| Eugenol | 0.5% |
| DB-31 Silicone Antifoam | 0.01% |

The above formulation is agitated and heated to 95° C. and formed a clear solution with slight foaming. When impregnated into a cellulosic absorbent pad this composition removed odors from a surrounding atmosphere.

EXAMPLE 6

The following formulation was prepared by mixing and heating the components to 95° C.

| Glycerine | 35% |
|---|---|
| Diethylene Glycol | 30% |
| Triethylene Glycol | 15% |
| Clindrol 200-0 | 10% |
| Propylene Glycol | 9.99% |
| Silicone Antifoam DB-31 | 0.01% |

10 grams of the above formula was impregnated into a 3 and ½ inch disc of 0.16″ filter material. A Petri dish was filled with 30 grams of calcium chloride and a trace of Rhodamine B. The disc and filter material was attached to the top of the Petri dish with Elmer's glue. This device pulled moisture through the impregnated filter material and removed odors from the surrounding environment.

EXAMPLE 7

The formulations set forth in Table III were prepared and 10 grams were impregnated into a cellulosic material made by Filter's Material, Inc. and placed in an air freshener package as described in Ser. No. 4104, filed Jan. 17, 1979. The six packages were placed in a room at 80° F. with humidity control turned full on. Water was running down the floor and collecting on the walls and vegetables in the room after 2 days were beginning to rot. The room and a strong dill vegetable smell. After 3 days the packages were sealed and removed from the room and taken to 7 people who were asked to rank the packages for strength of bad odor with 1 being very bad and 6 being the least. The average ranking is shown in Table III. The packages were then replaced in the room and a one-half pound piece of smoked fish was included in the test room. The odors increased to the point after 10 days of being very strong and the cabbage, cauliflower and broccoli were rotting and covered with mold. These packages were then again removed from the room and 8 different test subjects were asked to rate the packages. The relative average of ranking is shown in Table III. All of the examples, including the blank had a foul odor of the room. Furthermore, the presence of the Eugenol has some effect on the relative perception of odor absorption as runs A and C differed only in the inclusion of a small percentage of Eugenol.

TABLE III

| Run | 39-1 | D32-1 | 39-2 | 38-1 | 18-2 | |
|---|---|---|---|---|---|---|
| Component | A | B | C | D | Comparative | Blank |
| Propylene Glycol | 9.99 | 30.0 | 9.94 | 10.0 | 45.0 | — |
| Diethylene Glycol | 30.0 | 14.9 | 30.0 | 29.94 | 40.0 | — |
| Glycerin | 35.0 | 20.0 | 35.0 | 40.0 | 10.0 | — |
| Clindrol 200-0 | 10.0 | 5.0 | 10.0 | 5.0 | 5.0 | — |
| Tri Ethylene Glycol | 15.0 | 30.0 | 15.0 | 15.0 | — | — |
| Eugenol | — | 0.1 | 0.05 | 0.05 | — | — |
| DB-31 Anti Foam | 0.01 | — | 0.01 | 0.01 | — | — |
| Ave. Rank | | | | | | |
| 3 Day | 3.9 | 1.6 | 2.3 | 2.9 | 4.5 | 5.9 |
| 10 Day | 3.5 | 2 | 3.0 | 2.6 | 4.1 | 5.8 |

EXAMPLE 8

The formulas set forth in Table IV were prepared. One gram of each of these formulas was placed in a one inch square filterous material J-5 cotton patch. These cotton patches were placed in new one gallon paint containers along with a tenth of a gram of onion. The blank had a one inch square filter of material unimpregnated placed in the can with the onion. The cans were sealed ans smelled 24 hours later. The average ranking of the odor in the can is listed below with 1 being the strongest odor and 5 being the weakest odor. The blotters also were evaluated with 1 being the strongest odor and 5 being the weakest odor.

| Run | 146-1 | 146-2 | 39-1 | | |
|---|---|---|---|---|---|
| Component | A | B | C | Control | Blank |
| Glycerin | 40.0 | 37.0 | 35.0 | — | — |
| Diethylene Glycol | 35.0 | 33.0 | 30.0 | — | — |
| Triethylene Glycol | 15.0 | 15.0 | 15.0 | — | — |
| Propylene Glycol | 9.99 | 9.99 | 9.99 | — | — |
| DB-31 | 0.01 | 0.01 | 0.01 | — | — |
| Clindrol 200-0 | — | 5.0 | 10.0 | — | — |
| Water | — | — | — | 100 | — |
| Ave. Rank | | | | | |
| Can | 4.7 | 3.1 | 3.4 | 1.4 | 2.2 |
| Blotter | 2.6 | 4.0 | 2.4 | 2.8 | 3.2 |

EXAMPLE 9

The following formulation was prepared:

| Glycerine | 37% |
|---|---|
| Diethylene Glycol | 33% |
| Triethylene Glycol | 15% |
| Propylene Glycol | 9.99% |

| | |
|---|---|
| DB-31 Antifoam | 0.01% |
| WRS 1-66 | 5.0% |

Ten grams of the above material was placed in an open 4 ounce jar. This jar was placed in a 1 gallon glass jar along with 0.25 gram diethyl amino ethanol. The gallon jar was sealed with aluminum foil and a cap. After 24 hours the gallon jar was opened and the 4 ounce jar was sealed and removed. The material within the 4 ounce jar had the strong amine odor after 24 hours. The sealed 4 ounce jar, as well as a 4 ounce sample of the above formulation not exposed to the diethyl amino ethanol and a sample of diethyl amino ethanol all were run through a gascromatigram. The diethyl amino ethanol exhibited a characteristic peak at 267 while the sample of the above formulation exposed to the diethyl amino ethanol for 24 hours also exhibited a large peak in the same area at 271 characteristic of the diethyl amino ethanol. The unexposed sample, however, did not show any similar peak.

EXAMPLE 10

An experiment similar to that of Example 9 was conducted with the exception that 1 gram of the composition of Example 9 was impregnated onto a piece of #2 Whitman filer paper. This piece of filter paper was folded and placed standing in a 4 ounce jar. A similar piece of filter paper without any pretreatment was also placed in a 4 ounce jar. Both of these jars were placed in a 1 gallon glass jar along with 0.2 grams of diethyl amino ethanol. The jar was sealed for 24 hours and the filter paper was analyzed for the presence of diethyl amino ethanol along with a blank piece of filter paper not subjected to diethyl amino ethanol and a piece of filter paper containing 1 gram of the composition of Example 9 and not exposed to the diethyl amino ethanol. Upon analysis, the only sample showing any substantial quantity diethyl amino ethanol was that exposed to the diethyl amino ethanol and containing the 1 gram of the composition of Example 9. Both the blank filter paper exposed to the diethyl amino ethanol and the piece of filter paper containing the composition of Example 9 contained a small percentage of this material. However, this was far below the percentage contained within the example, including the composition of Example 9.

EXAMPLE 11

The following formula was prepared:

| Intermediate A | |
|---|---|
| Propylene Glycol | 9.94% |
| Diethylene Glycol | 30.0% |
| Glycerine | 35.0% |
| Clindrol 200-0 | 10.0% |
| Triethylene Glycol | 15.0% |
| Eugenol | 0.05% |
| DB-31 Antifoam | 0.01% |

Intermediate A is pressurized in an aerosol container having the following formulation:

| | |
|---|---|
| Intermediate A | 25.0% |
| Ethyl Alcohol (SD-40) | 25.0% |
| Propellent A-53 | 50.0% |

Three odor evaluation chambers were utilized. 45 grams of onion was chopped up and placed in each of these chambers for 30 minutes. The onion was then removed from the chambers and the above product was sprayed into one chamber. One chamber was left blank and the third was sprayed with a composition comprising 50% water and 50% A-53 propellent. Forty women were asked to open the small port door to each chamber and smell the contents and record their reactions. The composition of this example had significantly lower onion odor than either the water blank or the control and was overall liked as compared to the water blank and the control. These likes and dislikes were on a statistical basis at the 95% confidence level.

EXAMPLE 12

The formulas set forth in Table V were prepared. These formulas differ only in the particular acid utilized or in the case of Run D and E the same formula was utilized utilizing a different substrate base. A blank control was also run. These formulas were placed in a can along with a 0.10 gram of onion, 1 gram of water absorbed in a 1 square inch sheet of filter material and 1 gram of the composition shown in Table V was absorbed onto a similar 1 square inch sheet of filter material. These cans were randomized and exposed to 11 people who were asked to rank the cans in an order from 1 to 6 with the 1 being the strongest onion odor and 6 being the weakest. The sigma and the average for the 11 individuals is also shown in Table V.

TABLE V

| Run Component | A | B | C | D | E | Blank |
|---|---|---|---|---|---|---|
| Triethylene Glycol | 15.00 | 15.00 | 15.00 | 15.00 | 15.00 | |
| Propylene Glycol | 9.98 | 9.98 | 9.98 | 9.98 | 9.98 | |
| Diethylene Glycol | 33.00 | 33.00 | 33.00 | 33.00 | 33.00 | |
| Glycerine | 37.00 | 37.00 | 37.00 | 37.00 | 37.00 | |
| Clindrol 200-0 | — | 5.00 | 4.00 | 5.00 | — | |
| WRS-1-66 | 5.00 | — | — | — | 5.00 | |
| DB-31 Antifoam | 0.01 | 0.01 | 0.01 | 0.01 | 0.01 | |
| 10-Heptadecanoic Acid | — | — | 1.00 | — | — | |
| Palmitoleic Acid | — | — | — | 1.00 | — | |
| BHT | 0.01 | 0.01 | 0.01 | 0.01 | 0.01 | |
| Substrate Type Paper | X | X | X | X | — | — |
| S & L Acquell Sponge | — | — | — | — | X | — |
| Evaluation Results | | | | | | |
| Sum | 33.00 | 64.00 | 52.00 | 41.00 | 26.00 | 15.00 |
| Average | 3.00 | 5.80 | 4.70 | 3.70 | 2.40 | 1.40 |

I claim:
1. An odor absorbing composition comprising:
(a) from about 0.5 to 45% by weight of diethylene glycol;
(b) from about 0.5 to 45% by weight of propylene glycol;
(c) from about 0.5 to 30% by weight triethylene glycol;

(d) from about 1 to 50% by weight of glycerine;
(e) from about 0.1 to 20% by weight of a diethanol amide of a $C_{16}$ to $C_{18}$ unsaturated fatty acid, and
(f) from about 0.05 to 5% by weight of an unsaturated fatty acid.

2. An odor absorbing composition comprising:
(a) from about 10 to 35% by weight of diethylene glycol;
(b) from about 1 to 15% by weight of propylene glycol;
(c) from about 5 to 20% by weight of triethylene glycol;
(d) from about 10 to 40% by weight of glycerine;
(e) from about 1 to 7% by weight of a diethanol amide of a $C_{16}$ to $C_{18}$ unsaturated fatty acid, and
(f) from about 0.1 to 2% by weight of an unsaturated fatty acid.

3. The composition of claim 1 wherein the composition includes an effective amount of an anti-oxident.

4. The composition of claim 1 wherein the fatty acid is selected from the group consisting of palmitoleic acid, oleic acid, ricinoleic acid, hectadecanoic acid, linoleic acid, linolenic acid, eleosteric acid, lauroleic acid, myristoleic acid, and mixtures thereof.

5. The composition of claim 1 wherein the unsaturated acid is selected from the group consisting of oleic acid, recinoleic acid, hectadecanoic acid and mixtures.

6. The composition of claim 1 wherein the unsaturated acid is oleic acid.

7. The composition of claim 1 wherein the diethanol amide is selected from the group consisting of the diethanolamide of oleic acid, the diethanolamide of ricinoleic acid, the diethanolamide of hectodecanoic acid acid, the diethanolamide of mixed $C_{16}$–$C_{18}$ unsaturated fatty acids and mixtures thereof.

8. The composition of claim 1 wherein the diethanolamide is the diethanolamide of oleic acid.

9. An aerosol composition which comprises from about 1 to 30% by weight of the composition of claim 1; from about 10 to 70% by weight of a diluent; and from about 5 to 80% by weight of a propellent.

10. A solid air treating composition which comprises an absorbent substrate containing from 10 to 200% by weight based on the weight of the substrate of the composition of claim 1.

* * * * *